United States Patent
Johansson et al.

(10) Patent No.: US 10,932,893 B2
(45) Date of Patent: Mar. 2, 2021

(54) ORAL CARE DEVICE WITH SACRIFICIAL ELECTRODE

(71) Applicant: Colgate-Palmolive Company, New York, NY (US)

(72) Inventors: Patrik Johansson, Hoboken, NJ (US); Gerald Gontarz, Spotswood, NJ (US)

(73) Assignee: Colgate-Palmolive Company, New York, NY (US)

(*) Notice: Subject to any disclaimer, the term of this patent is extended or adjusted under 35 U.S.C. 154(b) by 124 days.

(21) Appl. No.: 16/215,236

(22) Filed: Dec. 10, 2018

(65) Prior Publication Data
US 2019/0110876 A1    Apr. 18, 2019

Related U.S. Application Data

(63) Continuation of application No. 14/983,724, filed on Dec. 30, 2015, now Pat. No. 10,179,038.

(51) Int. Cl.
*A61C 19/06* (2006.01)
*A61N 1/05* (2006.01)
(Continued)

(52) U.S. Cl.
CPC .......... *A61C 19/06* (2013.01); *A46B 15/0024* (2013.01); *A61C 17/005* (2013.01);
(Continued)

(58) Field of Classification Search
CPC ..... A61C 19/06; A61C 19/063; A61C 17/005; C25B 11/00; C25B 1/00; C25B 11/02; A45B 15/0024; A61N 1/0548
(Continued)

(56) References Cited

U.S. PATENT DOCUMENTS 2,998,893 A * 9/1961 Thomas ............... B67D 3/0045
                                              215/321
4,969,868 A    11/1990 Wang ................. A46B 15/0002
                                              15/167.1
(Continued)

FOREIGN PATENT DOCUMENTS

CA    2154860    1/1996
CN    2037169    5/1989
(Continued)

OTHER PUBLICATIONS

International Search Report of the International Searching Authority issued in International Application PCT/US2016/068691 dated Mar. 13, 2017.
(Continued)

*Primary Examiner* — Rafael A Ortiz

(57) ABSTRACT

A container, a toothbrush, or a device including at least one sacrificial electrode. In one aspect, the container may include a body adapted to contain an oral care solution and a cap selectively removable from the body. The cap may include a cavity configured to contain a fluid, a first electrode comprising a sacrificial metal, a second electrode spaced from the first electrode, and an electrical connection electrically connecting the first electrode and the second electrode to a power source. Activation of the power source may generate an electric field between the first and second electrodes, thereby causing the sacrificial metal of the first electrode to release ions into the fluid in the cavity of the cap.

6 Claims, 8 Drawing Sheets

(51) Int. Cl.
*A61C 17/00* (2006.01)
*C25B 11/02* (2006.01)
*C25B 1/00* (2006.01)
*A46B 15/00* (2006.01)

(52) U.S. Cl.
CPC .......... *A61C 19/063* (2013.01); *A61C 19/066* (2013.01); *A61N 1/0548* (2013.01); *C25B 1/00* (2013.01); *C25B 11/02* (2013.01)

(58) Field of Classification Search
USPC .................................................. 206/210, 83
See application file for complete search history.

(56) References Cited

U.S. PATENT DOCUMENTS

| | | | |
|---|---|---|---|
| 5,372,501 A | 12/1994 | Shalvi | A61N 1/322 132/321 |
| 5,824,292 A | 10/1998 | Carr et al. | |
| 5,921,251 A | 7/1999 | Joshi | A46B 15/0002 132/112 |
| 6,135,126 A | 10/2000 | Joshi | |
| 6,341,400 B1 | 1/2002 | Kobayashi | A46B 15/0002 15/105 |
| 6,955,538 B1 | 10/2005 | Borch | A61C 19/06 424/435 |
| 7,077,937 B2 | 7/2006 | Weres et al. | |
| 7,479,133 B2 | 1/2009 | Sun et al. | |
| 7,857,620 B2 | 12/2010 | Shih | A61C 1/088 15/167.1 |
| 8,156,599 B2 | 4/2012 | Waguespack | |
| 8,156,602 B2 | 4/2012 | Cai | |
| 8,398,325 B2 | 3/2013 | Gatzemeyer | |
| 8,708,700 B2 | 4/2014 | Russell | |
| 9,192,762 B2 | 11/2015 | Doll | A61N 1/32 |
| 9,445,661 B2 | 9/2016 | Wu | |
| 9,445,878 B2 | 9/2016 | Jimenez | |
| 10,307,235 B2 | 6/2019 | Jimenez | |
| 10,660,736 B2 | 5/2020 | Jimenez | |
| 2006/0070195 A1 | 4/2006 | Morita | A46B 15/0016 15/105 |
| 2007/0212665 A1 | 9/2007 | Jimenez et al. | |
| 2008/0003540 A1 | 1/2008 | Khawaled | |
| 2009/0070949 A1 | 3/2009 | Sagel | A46B 11/0058 15/28 |
| 2011/0245755 A1 | 10/2011 | Eischen | A61N 1/30 604/20 |
| 2012/0096657 A1 | 4/2012 | So | A46B 15/0024 15/105 |
| 2013/0071805 A1 | 3/2013 | Doll et al. | |
| 2013/0224679 A1 | 8/2013 | Teggatz | |
| 2015/0105712 A1 | 4/2015 | Pongpeerapat | A61K 9/0009 604/20 |
| 2015/0297500 A1 | 10/2015 | Robinson | |
| 2016/0184065 A1 | 6/2016 | Johansson | A61C 17/22 433/216 |
| 2017/0360973 A1* | 12/2017 | Saue | A61C 17/3481 |

FOREIGN PATENT DOCUMENTS

| | | |
|---|---|---|
| CN | 2545217 | 4/2003 |
| CN | 1468199 | 1/2004 |
| CN | 101355891 | 1/2009 |
| EP | 1508323 | 2/2005 |
| EP | 1651309 | 5/2006 |
| JP | 2015080489 | 4/2015 |
| KR | 20130034965 | 4/2013 |
| RU | 2223686 | 2/2004 |
| RU | 2373156 | 11/2009 |
| RU | 2449718 | 5/2012 |
| WO | 1997/07061 | 2/1997 |
| WO | 2001/30198 | 5/2001 |
| WO | 2001/85056 | 11/2001 |
| WO | 2002/40750 | 5/2002 |
| WO | 2007/047568 | 4/2007 |
| WO | WO 2009/066647 | 5/2009 |
| WO | 2014/042665 | 3/2014 |
| WO | 2014/088575 | 6/2014 |
| WO | 2016/106223 | 6/2016 |
| WO | WO 2016/087675 | 6/2016 |
| WO | 2017/116400 | 7/2017 |

OTHER PUBLICATIONS

Partial International Search Report of the International Searching Authority issued in International Application PCT/US2016/068691 dated Mar. 13, 2017.

* cited by examiner

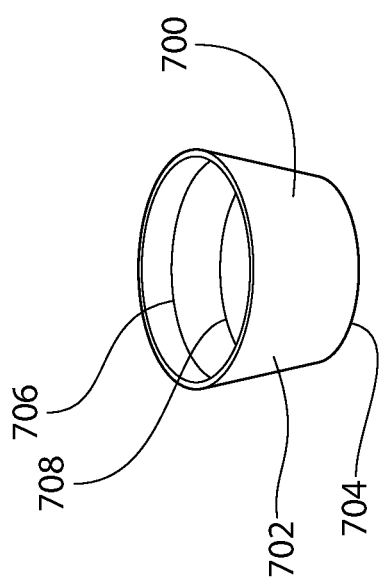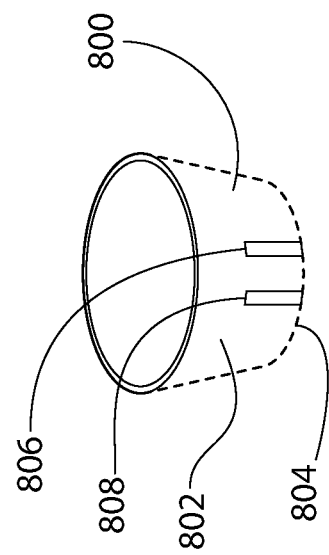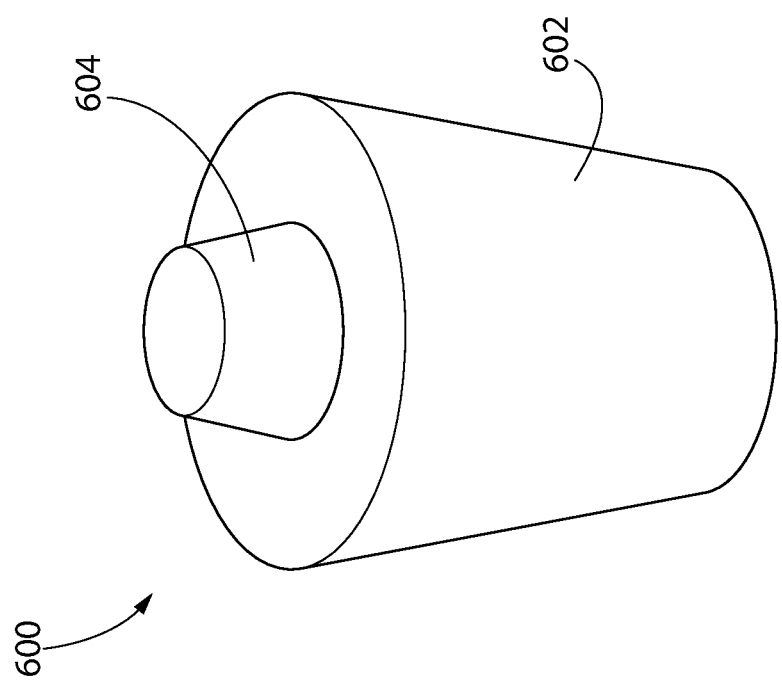

US 10,932,893 B2

ORAL CARE DEVICE WITH SACRIFICIAL ELECTRODE

CROSS-REFERENCE TO RELATED APPLICATIONS

The present application is a continuation of U.S. patent application Ser. No. 14/983,724, filed Dec. 30, 2015, the entirety of which is incorporated herein by reference.

BACKGROUND

Various oral care implements, such as toothbrushes, dental trays, and dental strips, are conventionally known. Such implements often act as a carrier for a dentifrice, which may be provided as a paste, gel, powder, liquid or some other composition. It is also conventionally known to provide one or more active ingredients in the dentifrice to achieve different oral health benefits. For example, conventional dentifrices may include ingredients that freshen breath, others that enhance tooth whitening, and/or still others that kill bacteria. However, it would be desirable to provide an oral care implement that can provide oral health benefits in addition to the separate dentifrice or without the requirement for the separate dentifrice.

Accordingly, there is a need in the art for an oral care implement that provides oral health benefits without or in addition to a dentifrice solution.

For example, there is a need in the art for an oral care implement that can generate ions in the head of the toothbrush, which may be used to promote oral health from within the oral cavity.

BRIEF SUMMARY

This application describes improved oral care implements, containers, or other devices that incorporate one or more electrode pairs. Within each electrode pair, a sacrificial metal is used that breaks down when a potential difference is applied across the electrode pair. Ions are released when the metal breaks down, and those ions aid in oral health.

In one aspect, the invention may be a container comprising: a body adapted to contain an oral care solution; and a cap selectively removable from the body, wherein the cap comprises: a cavity configured to contain a fluid; a first electrode comprising a sacrificial metal; a second electrode spaced from the first electrode; and an electrical connection electrically connecting the first electrode and the second electrode to a power source; and wherein activation of the power source generates an electric field between the first and second electrodes, thereby causing the sacrificial metal of the first electrode to release ions into the fluid in the cavity of the cap In another aspect, the invention may be an oral care device configured for placement in an oral cavity comprising: a base layer having a longitudinal axis; a power source disposed on a surface of the base layer; and an electrode layer disposed on the surface of the base layer or on a surface of the power source, the electrode layer comprising a first electrode comprising a first metallic strip electrically connected to the power source and a second electrode comprising a second metallic strip electrically connected to the power source and substantially parallel to the first metallic strip, wherein the electrode layer is disposed such that a length of the first electrode and a length of the second electrode are substantially parallel to the longitudinal axis of the base layer In yet another aspect, the invention may be a toothbrush comprising: a head; a plurality of tooth cleaning elements extending from the head; a first pair of electrodes coupled to the head, the first pair of electrodes comprising a first electrode and a second electrode, at least one of the first and second electrodes being a first sacrificial electrode; a second pair of electrodes coupled to the head, the second pair of electrodes comprising a third electrode and a fourth electrode, at least one of the third and fourth electrodes being a second sacrificial electrode; a power source operably coupled to the first and second electrodes and to the third and fourth electrodes to supply a current to the first and second electrodes and to the third and fourth electrodes, thereby causing the first and second sacrificial electrodes to release ions; and wherein the first sacrificial electrode comprises a first sacrificial metal and the second sacrificial electrode comprises a second sacrificial metal Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 6 is a perspective view of a container for a dentifrice solution according to another example implementation of this disclosure;

FIG. 7 is a perspective view of a cap, such as a cap for the container illustrated in FIG. 6, according to an implementation of this disclosure;

FIG. 8 is a perspective view of a cap, such as a cap for the container illustrated in FIG. 6, according to another implementation of this disclosure;

DETAILED DESCRIPTION

This description of presently preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

This disclosure relates generally to oral care implements, and more particularly to implements configured to include electrodes connected to a power source. Some examples of the following detailed description may generally refer to embodiments of the inventive implements in the context of a toothbrush, but the disclosure is not limited to toothbrushes; other oral care implements may also incorporate features of this disclosure. By way of non-limiting example, and as will be described in some examples below, mouth guard- and tray-type oral care implements and oral strips which do not include a handle, are known, and aspects of this disclosure may be incorporated into such implements. Moreover, features of the disclosure may be incorporated into other oral health-related applications.

Figure 1:
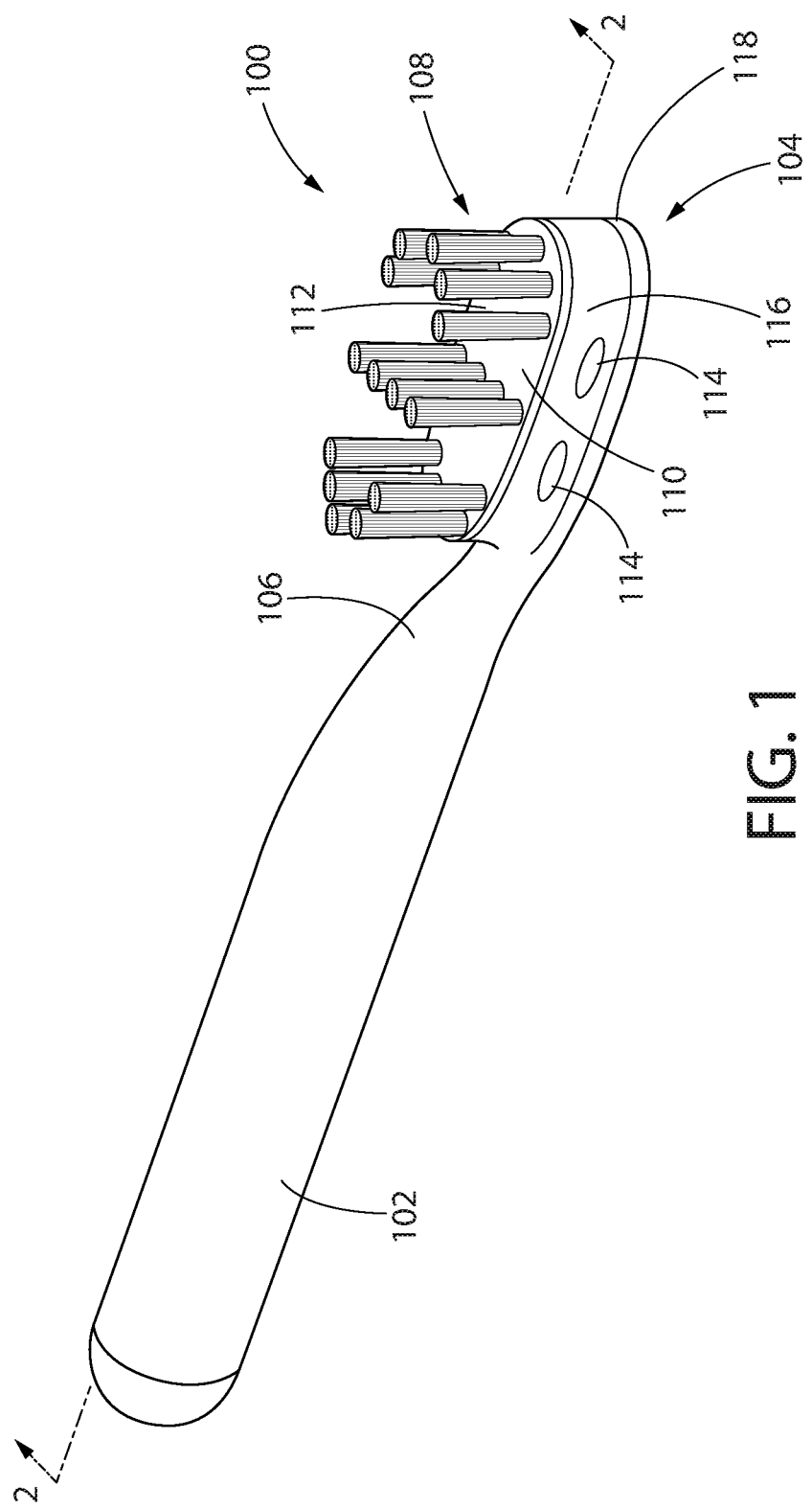
FIG. 1 is a perspective view of an oral care implement, embodied as a toothbrush, according to an example implementation of this disclosure.

FIG. 1 illustrates a toothbrush 100 according to a first implementation of this disclosure. The toothbrush 100 generally includes a handle 102, a head 104 disposed at the distal end of the handle 102, and a neck portion 106 generally disposed between the handle 102 and the head 104. As illustrated, the handle has a generally elongate shape, along a longitudinal axis. This disclosure is not limited to the shape and/or size of the toothbrush 100 illustrated in FIG. 1. In alternative implementations, one or more of the handle 102, head 104, and/or neck 106 may have different shapes, sizes, orientations, and/or the like. Additional features may also be incorporated into the toothbrush or disposed on the toothbrush.

In the embodiment illustrated in FIG. 1, the head 146 of the toothbrush 100 also includes a plurality of tooth cleaning elements 108 disposed on a tooth cleaning element support 110. As used herein, the term "tooth cleaning elements" includes any type of structure that is commonly used for or is suitable for use in providing oral health benefits (e.g., tooth cleaning, tooth polishing, tooth whitening, massaging, stimulating, etc.) by making intimate contact with portions of the teeth and/or gums. Such tooth cleaning elements include but are not limited to tufts of bristles that can be formed to have a number of different shapes, sizes and relative configurations, massage elements, and elastomeric cleaning members that can be formed to have a number of different shapes and sizes, or a combination of both tufts of bristles and elastomeric cleaning members. The tooth cleaning elements 108 may be arranged on the tooth cleaning element support 110 in many configurations.

In FIG. 1, the tooth cleaning elements 108 include bristles, which may be formed as bristle tufts. The tufts may be formed with bristles of the same or different bristle materials (such as nylon bristles, spiral bristles, rubber bristles, etc.). Moreover, while the tooth cleaning elements 108 may be arranged so that they are generally perpendicular to a top surface 112 of the tooth cleaning element support 110, some or all of the tooth cleaning elements may be angled with respect to that surface and/or with respect to each other. When the tooth cleaning elements 108 includes bristle tufts, it is thereby possible to select the combination of bristle configurations, bristle materials and/or bristle orientations to achieve specific intended results and operational characteristics, thus maximizing and enhancing cleaning, tooth polishing, tooth whitening, massaging, stimulation, and the like.

The tooth cleaning elements 108 may be attached to the tooth cleaning element support 110 by any conventional method. In certain embodiments, the tooth cleaning element support 110 may comprise a head plate having a plurality of holes formed there through, and the tooth cleaning elements may be mounted to the head plate within the holes. This type of technique for mounting the tooth cleaning elements to a head plate as the tooth cleaning element support 110 is generally known as anchor free tufting (AFT). In AFT a head plate or membrane is created and the tooth cleaning elements (such as bristles, elastomeric elements, and combinations thereof) are positioned into the head plate so as to extend through the holes of the head plate. The free ends of the tooth cleaning elements on one side of the head plate perform the cleaning function. The ends of the tooth cleaning elements on the other side of the head plate are melted together by heat to be anchored in place. As the tooth cleaning elements are melted together, a melt matte is formed, which is a layer of plastic formed from the collective ends of the tooth cleaning elements that connects the tooth cleaning elements to one another on one side of the head plate and prevents the tooth cleaning elements from being pulled through the tuft holes.

In some conventional designs, such as some conventional manual toothbrushes, after the tooth cleaning elements are secured to the head plate, the head plate may be secured to the head 104, such as by ultrasonic welding. When the head plate is coupled to the head 104, the melt matte is located between a lower surface of the head plate and a floor of a basin or cavity of the head 104 in which the head plate is disposed. The melt matte, which is coupled directly to and in fact forms a part of the tooth cleaning elements, prevents the tooth cleaning elements from being pulled through the holes in the head plate thus ensuring that the tooth cleaning elements remain attached to the head plate during use of the oral care implement.

In another embodiment, the tooth cleaning elements may be connected to a head plate or membrane later incorporated using a technique known in the art as AMR. In this technique, a head plate is provided and the bristles are inserted into holes in the head plate so that free/cleaning ends of the bristles extend from the front surface of the head plate and bottom ends of the bristles are adjacent to the rear surface of the head plate. After the bristles are inserted into the holes in the head plate, the bottom ends of the bristles are melted together by applying heat thereto, thereby forming a melt matte at the rear surface of the head plate. The melt matte is a thin layer of plastic that is formed by melting the bottom ends of the bristles so that the bottom ends of the bristles transition into a liquid, at which point the liquid of the bottom ends of the bristles combine together into a single layer of liquid plastic that at least partially covers the rear surface of the head plate. After the heat is no longer applied, the melted bottom ends of the bristles solidify/harden to form the melt matte/thin layer of plastic. In some conventional applications, after formation of the melt matte, a tissue cleaner is injection molded onto the rear surface of the head plate, thereby trapping the melt matte between the tissue cleaner and the rear surface of the head plate. Other structures may be coupled to the rear surface of the head plate to trap the melt matte between the rear surface of the head plate and such structure without the structure necessarily being a tissue cleaner. For example, in embodiments of this disclosure, a structure covering the melt matte may be a plastic material that is used to form a smooth rear surface of the head, or the like. In still other embodiments, the structure can be molded onto the rear surface of the head plate or snap-fit (or other mechanical coupling) to the rear surface of the head plate as desired.

Of course, techniques other than AFT and AMR can be used for mounting tooth cleaning elements to the tooth cleaning element surface 110, such as widely known and used stapling/anchoring techniques or the like. In such embodiments the tooth cleaning elements may be coupled directly to the tooth cleaning element surface 110. Furthermore, in a modified version of the AFT process discussed above, the head plate may be formed by positioning the tooth cleaning elements within a mold, and then molding the head plate around the tooth cleaning elements via an injection molding process.

Moreover, in certain embodiments, the invention can be practiced with various combinations of stapled, IMT, AMR, or AFT cleaning elements. Alternatively, the tooth cleaning elements could be mounted to tuft blocks or sections by extending through suitable openings in the tuft blocks so that the base of the tooth cleaning elements is mounted within or below the tuft block. In still other embodiments, likely in which the tooth cleaning elements are not bristles, the tooth cleaning elements may be molded integrally with the tooth cleaning element surface 110.

A plurality of apertures 114 is also illustrated in FIG. 1. The apertures 114 are disposed through a sidewall 116 of the head 104 and provide a channel or passageway through the sidewall 104. Such a channel may allow for fluid communication between an inner cavity of the head 104 of the toothbrush 100 and the external environment. The cavity, which may be bounded by the tooth cleaning element support 110, the sidewall 104 and a base 118, will be discussed in more detail below.

In some embodiments of this disclosure, an electrode system is disposed in the cavity in the head 104. Providing electrical current to the electrode system may be useful to provide oral health benefits in addition to the benefits obtained by use of the tooth cleaning elements 108. The electrode system may be controlled, at least in part, by a user operating the toothbrush 100. For example, a user interface, embodied as a switch or button, may be provided on the handle 102.

Figure 2:
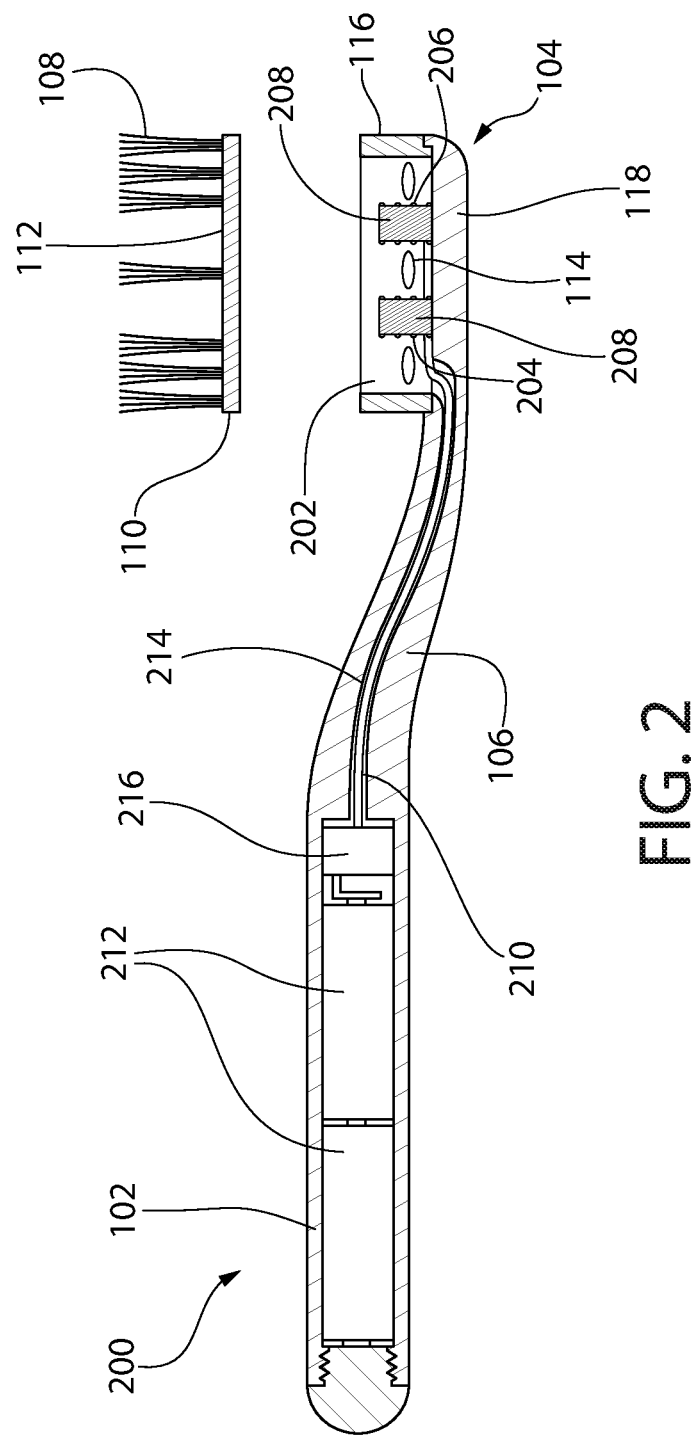
FIG. 2 is an exploded cross-sectional view of an example implementation of the toothbrush of FIG. 1, taken along section line 2-2 in FIG. 1.

FIG. 2 shows an exploded, cross-section of a toothbrush 200. The toothbrush 200 is an example implementation of the toothbrush 100. As illustrated, the head 104 of the toothbrush 200 includes a cavity 202. The cavity 202 is a basin or void defined by the sidewall 116 that extends upwardly from the base 118 of the head 104. A first electrode 204 and a second electrode 206 are disposed in the cavity 202. The electrodes 204, 206 may be any known shape or configuration, in addition to the configurations described in the examples herein. In the illustrated implementation, the electrodes 204, 206 are formed as electrical coils, and include a number of turns of a metallic wire. In the illustrated embodiment each of the electrodes 204, 206 includes such a winding, wound about a core 208. The cores 208 may be formed integrally with the base or may be formed separately and subsequently fixed to the base. In other embodiments, the cores 208 may not be present at all. Electrical or conductive leads 210 connect each of the electrodes 204, 206 to a power source 212. In the illustrated embodiment, the power source 212 is a plurality of batteries disposed in the handle 102 and the leads 210 extend from the electrodes 204, 206 through the neck 106 and into the handle 102 via a passageway or channel 214 connected to the cavity 202 of the head 104. In some embodiments the batteries may be replaced with some other power source, and the power source may be rechargeable.

As also illustrated, the tooth cleaning element support 110 is positioned relative to the head 104 to cover the cavity 202, thereby enclosing the electrodes 204, 206 in the cavity 202. In some implementations, the tooth cleaning element support 110 is fixed at a distal end of the sidewall 116, e.g., by an adhesive, welding, or other mechanical means.

Application of current to the electrodes 204, 206 creates an electrical field between the electrodes 204, 206. More specifically, the electrodes may be positioned to act as an anode and a cathode. The toothbrush may also include a controller and/or additional electronics 216. For example, the controller 216 may control current and/or voltage from the power source 212 to the electrodes 204, 206. In some embodiments, the controller may alternate the current through the electrodes 204, 206 and/or otherwise control the current, such as through pulse width modulation or alternating the current through the coils, to achieve desired activation sequences of the electrodes 204, 206. The controller 216 may also include a timing mechanism, such that the electrodes 204, 206 are activated for a predetermined time, for example.

In embodiments of this disclosure, at least one of the first electrode 204 and the second electrode 206 comprises a sacrificial electrode. A sacrificial electrode includes a sacrificial metal, and when current is applied between the first and second electrodes 204, 206, the sacrificial electrode gives up ions, e.g., by oxidizing. In one presently preferred embodiment, the sacrificial electrode includes zinc and the presence of an electrical potential oxidizes the zinc to release $Zn^{2+}$. Zinc ions are conventionally known to provide oral health benefits including e.g., anti-bacterial benefits. In this example, the zinc ions are given off in the cavity 202 of the head 104 of the toothbrush 200. Once released from the electrode to the cavity 202, the beneficial zinc ions enter the oral cavity via the apertures 114.

The apertures 114 also allow fluids, e.g., saliva and water, in the external environment to enter the cavity 202. Once in the cavity, the fluids act as an electrolyte to promote the release of the ions from the charged electrodes.

As noted above, in some embodiments the sacrificial metal may be zinc. When the electrode is a winding, as illustrated in FIG. 2, the wire comprising the winding may include zinc or a zinc alloy. In other embodiments, the electrodes may alternatively be formed as metal plates or other spaced-apart metal fixtures. Such other electrodes may also include zinc, zinc alloy, or some other sacrificial metal. In embodiments of this disclosure, zinc may comprise 90% or more of the metal making up the electrode, for example.

The description is not limited to the use of zinc and zinc alloys as the sacrificial electrode. In other implementations, for example, the sacrificial electrode may include different metals that can be oxidized to provide ions that give alternative oral benefits. For example, Tin ions, i.e., $Sn2+$ and $Sn4+$ have known oral health benefits and the sacrificial electrode could include Tin. Moreover, the oxidation of iron and/or manganese can drive the formation of hydroxide radicals from hydrogen peroxide, e.g., via the Fenton reaction, which may provide other benefits in the oral cavity.

Although one pair of electrodes is illustrated in FIG. 2, additional pairs of electrodes may also be present. For example, a first pair of electrodes may include zinc as a sacrificial metal, whereas a second pair of electrodes may include iron as a sacrificial metal. A controller such as the controller 216 may be used to individually power the pairs of electrodes, to provide varied oral care. In other implementations, multiple pairs of electrodes may include the same sacrificial metal, but the increased number will allow for release of additional ions.

Modifications to the toothbrush 200 described above are contemplated. For example, FIG. 3 illustrates a toothbrush 300 having a different electrode arrangement.

Figure 3:
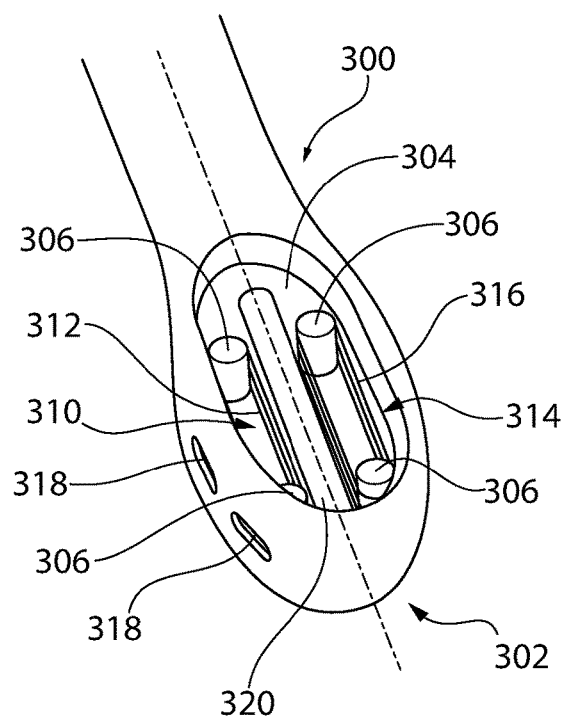
FIG. 3 is a partial perspective view of another example implementation of the toothbrush of FIG. 1.

More specifically, FIG. 3 illustrates that the toothbrush 300 includes a head 302 defining a cavity 304, similar to the cavity 202 described above. Four posts 306 are positioned in the cavity and extend from a bottom surface of the cavity 304. A first electrode 310 is formed as a series of windings 312 around a pair of the posts 306. A second electrode 314 is formed as a second series of windings 316 about the other two posts 306. Although not illustrated in FIG. 3, the first electrode 310 and the second electrode 314 are electrically connected to a power source. According to the arrangement of FIG. 3, the elongate windings 312, 316 provide increased surface area over the windings about a single post.

The toothbrush 300 functions in substantially the same manner as toothbrush 200 described above. That is, at least one of the electrodes 310, 314 preferably includes a sacrificial metal, such as zinc. When a potential is applied across the electrodes, the sacrificial metal oxidizes, releasing ions into the cavity 304. Apertures 318 are provided in the head 302 that allow for fluid flow between the cavity 304 and the external environment of the toothbrush 300. In this manner, as in the embodiment described above, released ions may exit the head 302 and provide a benefit in the external environment, e.g., the oral cavity. The apertures 318 also allow for the flow of fluids, such as saliva and/or water into the cavity 304, which fluids may act as an electrolyte to promote the oxidation of the sacrificial metal.

As also illustrated in FIG. 3, the toothbrush 300 may further include a barrier 320 disposed between the first electrode 310 and the second electrode 314. The barrier 320 may be any physical structure that will prevent migration of released ions. More specifically, when a zinc sacrificial electrode is used, the barrier 320 will prevent zinc ions released from the sacrificial electrode from migrating to the other electrode. Instead, the ions will remain suspended in the electrolyte, and eventually exit the head 302 via the apertures 318 to enter the oral cavity.

As noted above, a benefit of the configuration of the toothbrush 300 over that of the toothbrush 200 may be that each of the electrodes of the toothbrush 300 has an increased surface area versus that of the electrodes in the toothbrush 200. For example, in some embodiments, it may be desirable to provide each electrode with a surface area greater than about 1 cm$^2$ to produce sufficient ions for a desired oral benefit. For example, each electrode may be formed of 15 to 20 cm long wire having 0.25 to 0.5 mm diameter. Winding of any length of wire about two spaced posts will require fewer turns than winding about one post. As will be appreciated, the release of ions will be dependent upon a number of factors, including the surface area of the electrode, the purity of the material forming the electrode, a distance between the electrodes, and the like, and different configuration may be appropriate in different applications.

Figure 4:
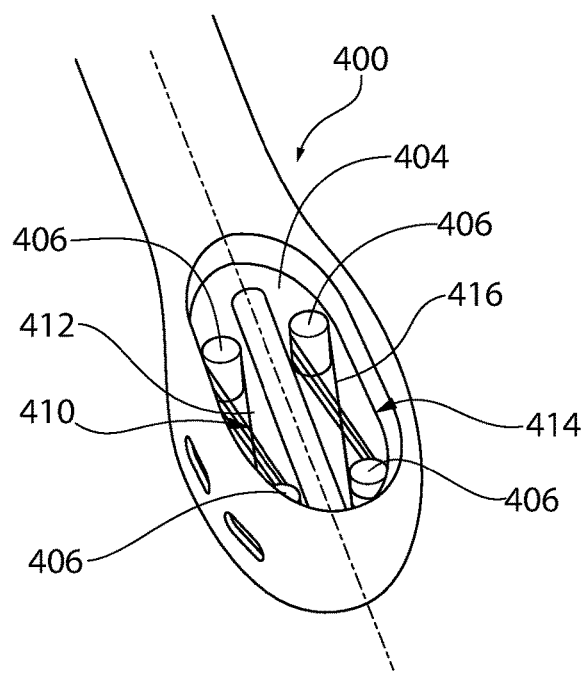
FIG. 4 is a partial perspective view of another example implementation of the toothbrush of FIG. 1.

Other electrode configurations also are contemplated. For example, FIG. 4 illustrates a toothbrush 400 having a cavity 404 in which a pair of electrodes 410, 414 is disposed. Each of the electrodes 410, 414 is wound about a pair of posts 406, similar to the embodiment of FIG. 3. However, the wire comprising the windings 412, 416 of each of the electrodes 410, 414 is wound in a FIG. 8 pattern. This configuration may allow for additional surface area of the electrode over the embodiment illustrated in FIG. 3, because it accommodates a longer length of wire in the same footprint. In each of FIGS. 3 and 4, the tooth cleaning elements are removed for clarity.

Those having ordinary skill in the art will understand that additional electrode configurations are possible. As noted above, one or both of the electrodes in an electrode pair may be formed as a metal plate or a thin metal strip, for example.

In some embodiments, the ions released by the electrodes may provide a direct oral care benefit, as in the case of zinc ions, which are known anti-bacterial agent. Conventionally, zinc ions have been formulated into a dentifrice or mouthwash for delivery into the oral cavity. However, aspects of the present disclosure allow for delivering free or weakly chelated zinc species directly into the oral cavity. Moreover, the zinc species may be delivered into a non-therapeutic dentifrice or mouthwash. That is, the benefits of zinc ions may be realized without the need for a specific dentifrice including the zinc. According to aspects of this disclosure, a zinc electrode may be oxidized from its metal $Zn^0$ state to $Zn^{2+}$ state by the removal of electrodes electrochemically: $Zn \rightarrow Zn^{2+} + 2$ electrons.

Figure 5:
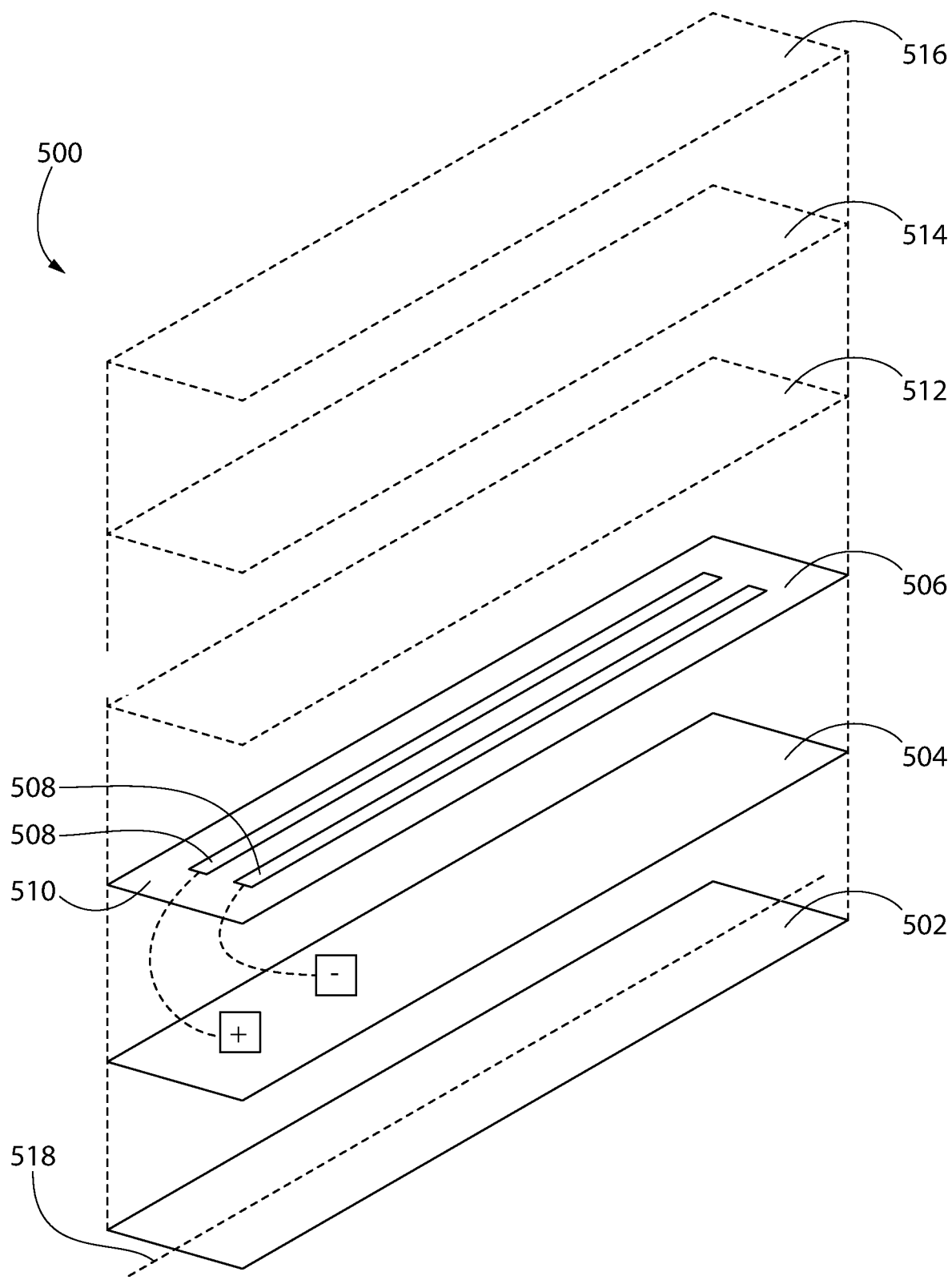
FIG. 5 is an exploded perspective view of an oral care implement, embodied as a dental strip or patch, according to another example implementation of this disclosure.

In addition to contemplating additional electrode arrangements in a toothbrush or similar device, the inventors also contemplate the use of electrode arrangements in different oral care devices. For example, FIG. 5 illustrates an oral care device 500 according to other implementations of this disclosure. More specifically, FIG. 5 is a schematic illustration of a plurality of layers or substrates that are stacked or otherwise disposed together to form a complete device 500. In embodiments of this disclosure, the device 500 is embodied as a strip or patch sized for placement in the oral cavity. The device 500 is illustrated in FIG. 5 as having a generally rectangular shape, but this disclosure is not limited to rectangular forms. For example, the size and/or shape of the footprint of the device 500 may be varied depending upon such factors as the application, desired aesthetics, or manufacturability concerns. The strip is preferably between about 1 mm and about 5 mm thick, and more preferably about 1.5 mm to about 3 mm thick. The reduced thickness may result in more comfort for a user of the device, and may promote flexure or bending of the device, e.g., to better conform to the contours of the oral cavity.

As illustrated, the oral care device 500 includes a base layer 502, a power source 504, and an electrode layer 506. Other layers, which may include a covering 512, an adhesive layer 514, and a release layer 516 also are illustrated in phantom lines in FIG. 5. One or more of these layers may be included in various embodiments of this disclosure.

The base layer 502 is preferably a thin, flexible substrate. The substrate may be made from any number of orally acceptable materials, including but not limited to, textiles, cloth, wood composite, resin, elastomer, paper, insoluble or less soluble cellulose derivatives such as ethyl cellulose and cellulose acetate, polyvinyl chloride, wax, Parafilms™, polyethylene, polyvinyl alcohol, Teflon™, polyvinyl chloride, polyvinyl acetate and their derivatives. In some instances, the flexible substrate may also or alternatively include a water-soluble polymer to promote adhesion of the device 500 to the teeth or gums. For example, the base layer 502 may include hydrophilic cellulose ethers (e.g. carboxymethyl cellulose, hydroxypropyl cellulose, hydroxypropyl methylcellulose), polyvinyl acetates, carbomers (e.g., Carbopol 97 IP), polysaccharide gums (e.g. xanthan gum), modified food starches, gelatin (e.g. animal or fish-based gelatin), cross-linked carboxyvinyl copolymers, cross-linked polyvinylpyrrolidones, polyethylene oxide (e.g., Polyox), polyacrylic acids and polyacrylates, polyvinyl alcohols, alginate, casein, pullulan, and combinations thereof.

The power source 504 is disposed on the base substrate 502, and may be a battery. The power source may be single use or rechargeable. Although several types of batteries, including button and coin batteries, may be used in accordance with principles of this disclosure, in some preferred embodiments the power source 504 comprises a flexible power source, such as a polymer battery. Polymer batteries may be preferred for their thin profile and/or their flexibility. For instance, polymer batteries may be as thick as 750 microns, or thinner. The power source 104 may be a printed battery such as a battery commercially available from Imprint Energy, Inc. of Alameda, Calif. The printed battery may include a metal screen-printed on a flexible substrate, for example.

In some embodiments, the power source 504 may be adhered to the base substrate using any known adhesive, epoxy, or the like. Alternatively, the power source 504 may include the base substrate 502. For example, some commercially available polymer batteries generally include components printed on a substrate. When such a commercially available battery is used in embodiments of this disclosure, the substrate of the battery may also act as the base substrate 502.

The electrode layer 506 generally includes a pair of electrodes 508 disposed on an electrode substrate 510. As illustrated, the electrodes 508 may be formed as two spaced-apart conductive strips functioning as an anode and a cathode with applied current. The electrodes 508 are substantially parallel and extend generally longitudinally, i.e., parallel to a longitudinal axis 518 of the device 500. The electrodes are sufficiently thin that they can bend with, e.g., without delaminating from, the base layer 502 and the electrode substrate. The electrodes 508 may be printed or otherwise formed on the electrode substrate 510 and may comprise any number of materials including, but not limited to, tin, silver, copper, platinum, and the like. The materials comprising the electrodes preferably are chosen for their flexibility, as well as for their compatibility with the environs of the oral cavity. Also, in embodiments of this disclosure, at least one of the electrodes 508 may be formed from a sacrificial material, such as a sacrificial metal. For example, as described above, an electrode made of zinc will oxidize upon application of current, thereby releasing $Zn^{2+}$. These zinc ions are recognized as effective anti-bacterial agents.

The electrodes 508 are attached to terminals of the power source 504. In some embodiments, the electrode 508 may be connected to the power source 504 using leads or similar conductors. In still other embodiments, the electrode layer 506 may be affixed on the power source 504 in such a manner as to create an electrical communication between the electrode 508 and the power source 504. In still other embodiments, the power source 504 and the electrodes 508 may be disposed on a common substrate, such as the base substrate 502 or the electrode substrate 510.

Although two electrodes 508 are illustrated in FIG. 1, additional electrodes 508 may also be provided. For example, the electrodes may be positioned and numbered generally to correspond with a location and number of a user's teeth. Moreover, the electrodes may be arranged generally perpendicularly relative to the axis 516.

The device 500 comprising the base substrate 502, the power source 504, and the electrode layer 506 may form a complete oral care device 500. In operation, the oral care device 500 may be placed in a user's oral cavity and current is passed through the electrodes 508 to provide an electrochemical benefit in the oral cavity. As discussed above, the benefit may constitute release of ions or the like upon degradation of the electrode 508. To promote the release of ions, the electrodes may be exposed to the environs of the oral cavity, e.g., such that saliva can act as an electrolytic solution. Alternatively, the covering 512 may be disposed over the electrodes, such that the electrodes are sandwiched between the covering and the electrode substrate. In this manner, the electrode substrate 510 and the covering 512 form a housing containing the electrodes. The covering 512 and/or the electrode substrate 510 may be formed to allow migration of saliva or other fluids therethrough, and into contact with the electrodes. For example, pores or openings may be formed through one or both of the electrode substrate and the covering 512. Moreover, the covering may be affixed to the substrate only about a periphery of the covering, thereby allowing for a volume around the electrodes. The interface between the electrode substrate and the covering may also be a discontinuous attachment, creating openings or voids through which fluid can enter and leave the volume.

While the device 500 may be complete with the base substrate 502, the power source 504, the electrode layer 506, and optionally the covering 512, one or more optional components may also be included. For example, the device 500 may also or additionally include an adhesive layer 514, to promote retention of the device 500 in a desired position in the oral cavity. The adhesive layer may include any conventional orally-compatible, releasable adhesive. For example, water-soluble polymers, noted above as an example of a base layer substrate, may also be used as an adhesive in the present disclosure. As illustrated in FIG. 5, the adhesive layer 514 may have the same general footprint as the other components making up the strip. As a result, the entire strip may include adhesive. In other embodiments, less adhesive may be included. For example, only portions of the footprint of the strip may be adhesive. For instance, adhesive may be provided only at longitudinal ends of the strip, with the strip being applied much like other commercially available bandages. In other implementations, adhesive may be applied about the periphery of the strip and in still other embodiments the adhesive layer may include a plurality of adhesion points or regions.

The oral care device 500 may also include a release layer 516. The release layer 516 may be a removable member disposed over components of the device 500, for example to prevent contamination of the oral care device 100 prior to insertion into the mouth. The release layer 516 illustrated in FIG. 5 comprises a thin sheet of flexible material, e.g., a polymeric material, that a user peels off to reveal the electrode layer, covering and/or adhesive layer, depending upon the construction of the device 500. When the adhesive layer 514 is present, for example, the release layer will ensure that the adhesive remains tacky until the device 500 is to be used. Although the release layer 516 is shown as a single layer, in other embodiments the release layer may instead take the form of an envelope or complete package, e.g., for completely retaining the oral care device 500 therein.

In some embodiments, the release layer 516 may also control activation of the device 500. For example, the release layer may include a physical obstruction that prevents electrical communication between the power source 504 and the electrodes 508. Removing the release layer will also remove this obstruction, thereby allowing current to flow from the power source to the electrode 508. In other implementations, removal of the release layer 516 may be detected, e.g., using a presence/absence sensor, and the output from that sensor may trigger powering-up of the device.

Although not illustrated, the device 500 may also include control circuitry or similar features to control the electrical circuit created by the power source 504 and the electrode 508. For example, the control circuitry may alternate the polarity of the electrodes during use. Alternating the polarity may prevent accumulation of charged particles or ions on the electrodes. The control circuitry may also be programmed to control an amount of current supplied to the electrode 508. The control circuitry may also include a power-up function, or the like, to activate the power source when the device is ready for use. The control circuitry may include a manual switch as part of the power-up function, such as a toggle or push button switch. Moreover, as discussed above, the release layer could also be integrated into the power-up function, e.g., such that removal of the release layer powers up the device. In other embodiments, the control circuitry may include sensor outputs. For example, a conventional presence/absence sensor could be disposed to be covered by the release layer, and detect removal of the release layer. This detection could then be used to turn on the device. In another embodiment, a water- or liquid moisture-detecting sensor may be provided. When the sensor comes in contact with saliva, i.e., upon being inserted into the mouth, the power source is turned on. The control circuitry could be provided on a separate layer, or could be integrated into another layer. For example, it may be desirable to incorporate the control circuitry into the electrode layer, the base layer, and/or the power source layer.

As will be appreciated, the oral care device 500 is generally a thin, flexible device capable of simple insertion into the oral cavity. Depending upon the benefit to be achieved from the device, the device may be placed over one or more teeth, on the gums, on the inside of the cheek, and/or on or under the tongue. In some embodiments, it may be desirable to situate the electrodes as close to the teeth as possible. Because the device is flexible, in some examples the device can be folded, for example, proximate the longitudinal axis 518, such that device can be placed around one or more teeth with one of the electrodes 508 in front of the tooth/teeth and the other of the electrodes 508 disposed behind the tooth/teeth. In this manner, the electrical field generated at the electrodes 508 would pass through the tooth/teeth disposed between the spaced electrodes 508. This arrangement disposes the electrodes in intimate contact with the teeth. Such an arrangement may also be beneficial to drive ions released from the sacrificial electrode(s) into the tooth enamel.

In another, similar implementation, the oral care device may take the form of a molded tray. For example, the base substrate 502 may be relatively rigid, such as molded. In still further alternatives, the power source may be disposed outside the oral cavity and/or separate from the device 500, yet electrically connected to the electrodes. Other modifications will also be appreciated by those having ordinary skill in the art, with the benefit of this disclosure.

Yet other implementations of this disclosure are illustrated in FIGS. 6-8. FIG. 6 shows a container 600 for a dentifrice, which may be a liquid dentifrice, such as mouthwash or whitening solution, for example. The container 600 includes a body 602 and a cap 604 configured for selective placement on and removal from the body 602.

FIGS. 7 and 8 illustrate examples of the cap 604, as shown in FIG. 6. In FIG. 7, a cap 700 includes an annular sidewall 702 terminating at a closed end 704. The sidewall 702 and the closed end 704 define a volume. Threads (not shown) or another known mechanism may be provided on an inner surface of the sidewall 702 to promote attachment of the cap 702 to a container body. A first electrode 706 and a second electrode 708 also are disposed on the inner surface of the sidewall 702. The electrodes 706, 708 are illustrated as spaced-apart metallic windings fixed to the sidewall 702. Although not illustrated, a power source electrically connects the electrode 706, 708 to provide a potential difference between the electrodes. When the power source is activated, an electrical field is created between the electrodes. As in embodiments discussed above, one of the electrodes preferably is a sacrificial electrode, made of a sacrificial metal such as zinc.

The closed end 704 of the cap 700 is relatively flat, such that the cap 700 may be placed on a flat surface, with the closed end 704 resting on the surface. In this manner, the volume defined by the sidewall 702 and the closed-end 704, can hold a substance, such as the dentifrice carried in the container. In use, the cap 700 is filled with the dentifrice and power is applied across the electrodes 706, 708. The dentifrice acts as an electrolyte, and ions from the sacrificial metal comprising the sacrificial electrode are released into the dentifrice. A user then empties the contents of the cap 700 into his mouth so the ions may provide an oral benefit. This oral health benefit may be in addition to any benefit received from the dentifrice itself. In other uses, the cap 700 may be used separately from the dentifrice contained in the container. For example, the cap 700 with electrodes 706, 708 may be filled with water and ions from the electrodes may be released into the water. The user may then rinse with the ion-infused water to obtain an oral health benefit separate from the dentifrice.

Although the power source and electrical connections between the power source and the electrodes 706, 708 are not illustrated in FIG. 7, those components may be disposed proximate the closed end 704 of the cap 700. A false end or other substrate may be provided over the power source and/or electrical connections to ensure that fluid in the cap 700 does not contact those components. Similarly, it may be desirable to substantially shield the electrodes from the atmosphere. In one implementation, the sidewall 702 may comprise two concentric sidewalls with the electrodes disposed between the concentric walls. Thus, the user may grasp the outer sidewall when removing the cap from or placing the cap on the container while the inner sidewall is visible inside the cap. In this embodiment, the inner sidewall may be provided with apertures or other holes that allow for fluid flow into the space between the concentric sidewalls, such that the fluid contained in the cap may come into contact with the electrodes.

FIG. 8 is another example implementation of a cap 800, such as the cap 604 of FIG. 6. In this example, the cap 800 includes an annular sidewall 802 terminating at a closed-end 804, much like the embodiment illustrated in FIG. 7. Two electrodes 806, 808 are disposed to depend from the closed end 804 into a volume defined by the sidewall 802 and the closed-end 804. The electrodes 806, 808 are illustrated as parallel plates, although they may take other forms, including but not limited to the wound electrode configurations illustrated in preceding embodiments. As with previous embodiments, at least one of the electrodes is preferably a sacrificial electrode, formed of a sacrificial metal. Use of the cap 800 is similar to that of the cap 700 described above and will not be described again here.

Although not illustrated, the caps 700, 800 may also include a user interface, such as a button or switch that is pressed by a user to activate the electrodes. Control circuitry, which may include timing circuitry, may be provided to activate the electrodes for a predetermined amount of time, for example in response to user interaction with the user interface. The timing may be sufficient to release a predetermined amount of ions from the sacrificial electrode, for example. An indicator or the like, such as an indicator light or sound may also be provided to indicate to a user that the activation of the electrodes is complete.

Other modifications to the container and cap embodiment also are contemplated. For example, containers are known that have a separate reservoir proximate an open mouth of the container. In these containers, a user squeezes a main body of the container to move fluid to the reservoir. The reservoir may include gradations or other markings as visual indications of an amount of the fluid in the reservoir, for example. According to an embodiment of this disclosure, a pair of electrodes may be provided in the reservoir. Also, the power source and the electrical connections may be associated with the container body, instead of the cap.

The foregoing embodiments illustrate example devices related to oral health that incorporate electrodes. At least one of the electrodes is a sacrificial electrode, made of a sacrificial metal. For example, the sacrificial electrode may be made of zinc, which may be 90% or more pure zinc. When an electrical potential is produced across the electrodes, zinc ions are released into an electrolyte, which may be saliva, water, or a dentifrice. In embodiments of this disclosure, the electrolyte is then transferred to the oral cavity to provide a benefit to the oral cavity. For example, when zinc is used as the sacrificial metal, the electrolytic fluid will carry zinc ions, which act as an antibacterial agent in the oral cavity. Other sacrificial metals, such as iron, or tin, may also or alternatively be used, to provide other or additional oral benefits. When the electrolyte used is a dentifrice solution, such as a mouthwash or tooth whitening agent, the electrodes may also act to activate components in the dentifrice.

Although other or additional metals may be used in the sacrificial electrodes, the inventors have conducted a number of tests using zinc.

In one example test, a manual toothbrush (Colgate 360 toothbrush) was used to simulate brushing. Specifically, simulated brushing was performed in a 10 mL vial with 1 gram of great regular flavor toothpaste and 1 mL saliva. Also in the test, a toothbrush as illustrated in FIG. 4 was provided. Each of the electrodes of the toothbrush comprised zinc wire wound in a figure-eight about spaced posts. Simulated brushing also was performed using this toothbrush in a 10 mL vial with 1 gram of great regular flavor toothpaste and 1 mL saliva. The brushing using the toothbrush with electrodes was done with the brush in an OFF state as well as in an ON state. In the ON state, current was provided at approximately 2 mA and voltage was set to 2V.

Figure 9:
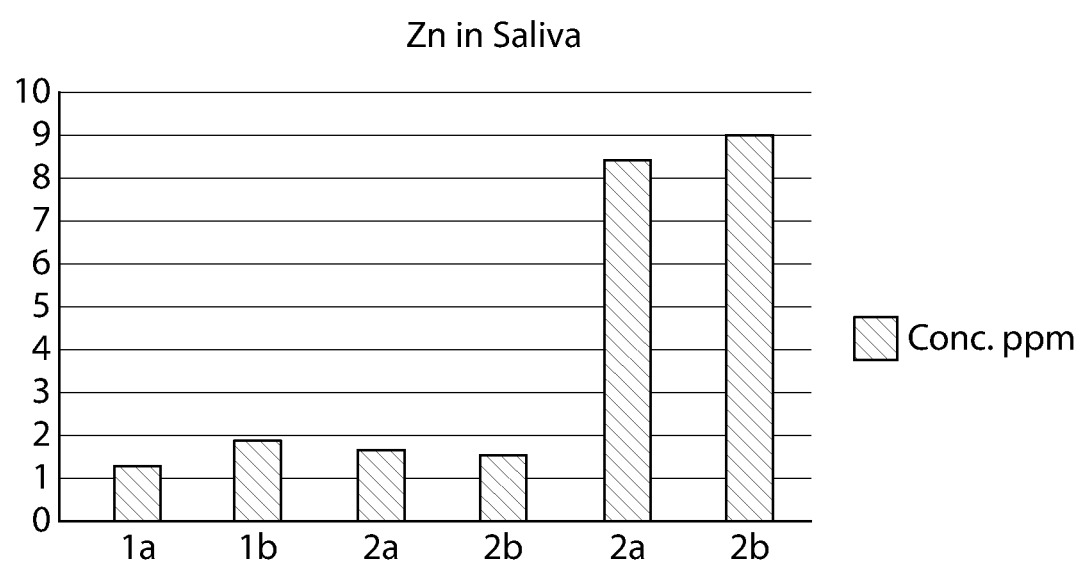
FIG. 9 is a graph illustrating the production of zinc ions using sacrificial electrodes according to example embodiments of this disclosure.

FIG. 9 shows the results of the just-described example test. Specifically, FIG. 9 illustrates a concentration of zinc in saliva (as parts per million) for two iterations of simulated brushing for each state, i.e., manual toothbrush, electrode toothbrush in OFF state, and electrode toothbrush in ON state. In this example, the samples were tested using inductively coupled plasma atomic absorption spectroscopy.

Figure 10:
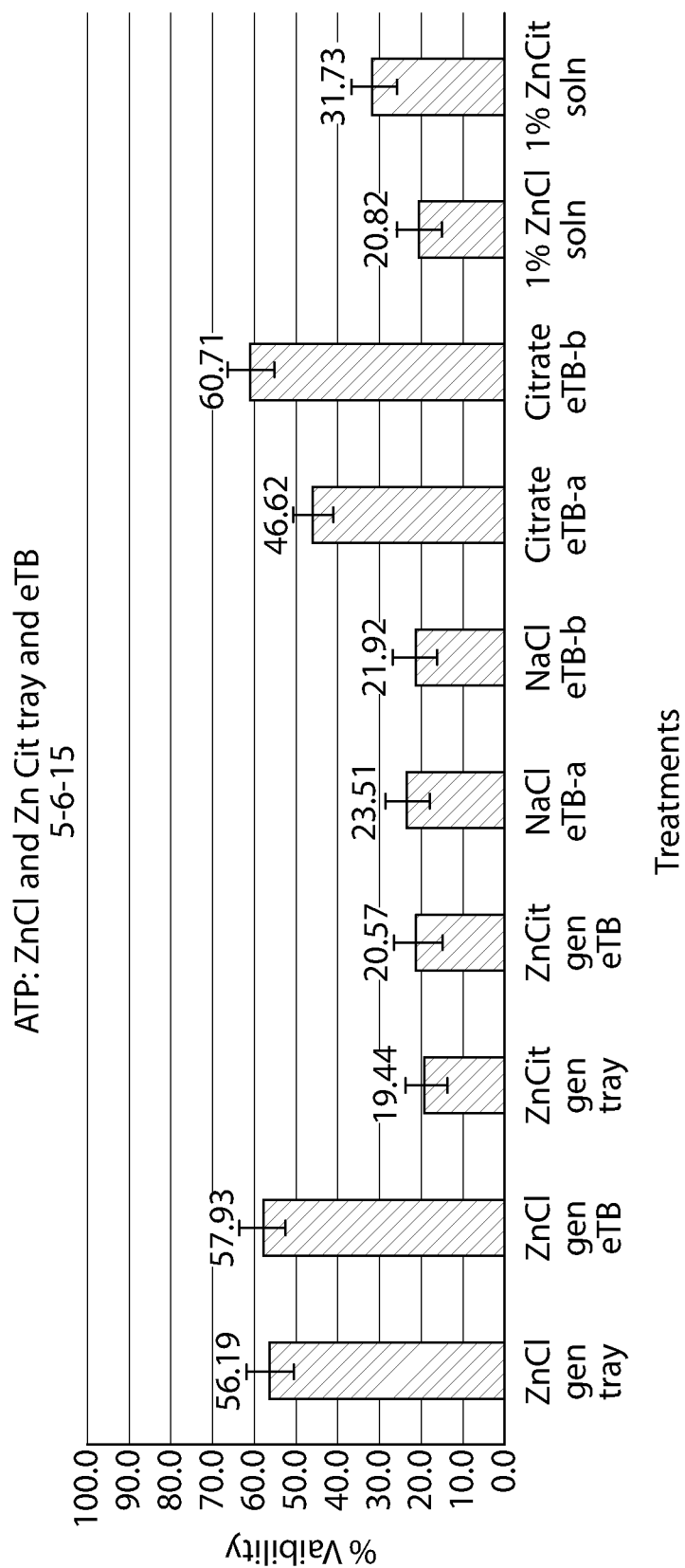
FIG. 10 is a graph illustrating viability data relating to an ATP assay test, using sacrificial electrodes according to example embodiments of this disclosure.
Figure 11:
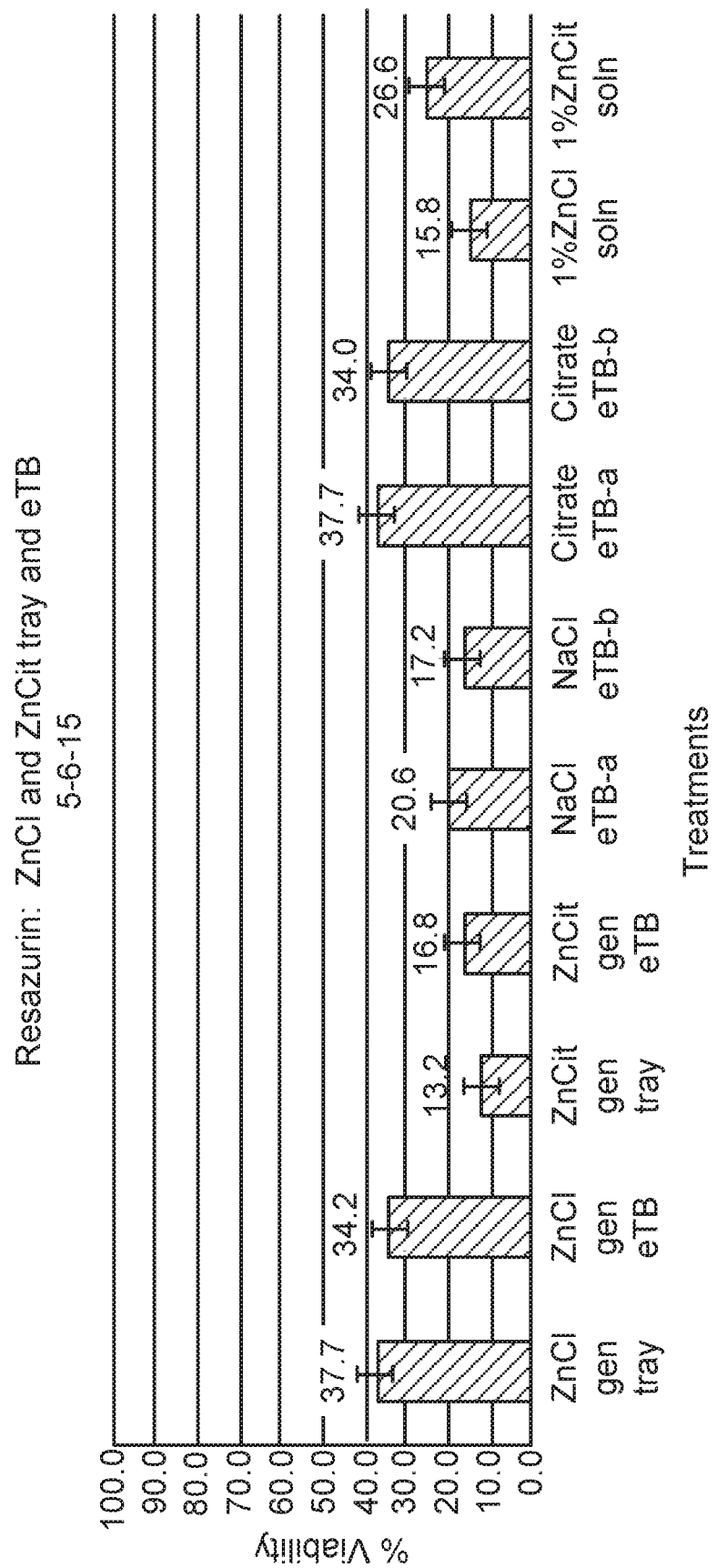
FIG. 11 is a graph illustrating viability data relating to a Resazurin assay test, using sacrificial electrodes according to example embodiments of this disclosure.

In additional tests, an ATP or bioluminescent assay and a Resazurin assay were completed for a strip (like that shown in FIG. 5), a tray and a toothbrush ("eTB"—as shown in FIG. 4). FIG. 10 shows the results of the ATP assay and FIG. 11 shows the results of the Resazurin assay. The Planktonic resazurin assay was used to determine the relative amount of bioactive metal compound in a formula. This assay uses a mixed species bacterial inoculum and the metabolic indicator dye resazurin is used as a measure of bacterial viability following treatment. The ATP or bioluminescent assay is used to measure total generic bacteria. For both assays the five species mix of planktonic bacteria (*Actinomyces viscosus, Lactobacillus casei, Streptococcus oralis, Veilonella parvula* and *Fusobacterium nucleatum*) is treated for one hour with the indicated dilution of dentifrice. Following treatment, the samples are washed and incubated with the non-fluorescent blue dye resazurin. When metabolically active cells reduce resazurin, it is converted to the pink fluorescent dye resorufin. The ATP assay uses the luciferin-luciferase ATP-dependent reaction to evaluate the viability of populations of organisms. By comparing the fluorescence of the test cultures to a standard curve, we can determine the percentage of the initial population of bacteria that remains viable after the one hour treatment.

The ATP viability data illustrated in FIG. 10 is also shown in Table 1:

TABLE 1

| ATP viability | |
|---|---|
| Product | % Viability |
| ZnCl gen tray | 56.19 |
| ZnCl gen eTB | 57.93 |
| ZnCit gen tray | 19.44 |
| ZnCit gen eTB | 20.57 |
| NaCl eTB-a | 23.51 |
| NaCl eTB-b | 21.92 |
| Citrate eTB-a | 46.62 |
| Citrate eTB-b | 60.71 |
| 1% ZnCl soln | 20.82 |
| 1% ZnCl soln | 31.73 |

The Resazurin viability data illustrated in FIG. 11 is also shown in Table 2:

TABLE 2

| Resazurin viability | |
|---|---|
| Product | % Viability |
| ZnCl gen tray | 37.71618426 |
| ZnCl gen eTB | 34.24028388 |
| ZnCit gen tray | 13.2054818 |
| ZnCit gen eTB | 16.81131976 |
| NaCl eTB-a | 20.64760777 |
| NaCl eTB-b | 17.23116481 |
| Citrate eTB-a | 37.74257346 |
| Citrate eTB-b | 33.95196444 |
| 1% ZnCl soln | 15.7617772 |
| 1% ZnCl soln | 26.64967783 |

The test results illustrated in FIGS. 10 and 11 and Tables 1 and 2 show that a tray, a strip and an electric toothbrush may be used to deliver zinc electrochemically. The zinc may enhance already existing products, including those whose original purpose may have been other than therapeutic.

The foregoing examples describe oral care implements incorporating a sacrificial electrode to release ions that provide benefits in the oral cavity. To the extent that some implementations contemplate placing electrical components and/or generating electrical fields in the oral cavity, it should be noted that the devices are operated with sufficiently low current and voltage that will not have an adverse effect to the oral cavity or the user. For example, currents are on the order of not more than 5 milliamps and voltages of no greater than about 3 Volts may be used to generate ions according to embodiments of this disclosure.

Although example embodiments have been described in language specific to the structural features and/or methodological acts, the claims are not necessarily limited to the specific features or acts described. Rather, the specific features and acts are disclosed as illustrative forms of implementing the example embodiments.

What is claimed is:

1. A container comprising;
a body adapted to contain an oral care solution; and
a cap selectively removable from the body, wherein the cap comprises:
   a cavity configured to contain a fluid;
   a first electrode comprising a sacrificial metal;
   a second electrode spaced from the first electrode; and
   an electrical connection electrically connecting the first electrode and the second electrode to a power source; and
wherein activation of the power source generates an electric field between the first and second electrodes, thereby causing the sacrificial metal of the first electrode to release ions into the fluid in the cavity of the cap; and
wherein the cap comprises a base surface forming a closed end of the cap and an annular sidewall extending from the base surface, and wherein the first and second electrodes extend from the closed end of the cap into the cavity.

2. The container according to claim 1 further comprising threads on the inner surface of the annular sidewall for coupling the cap to the body.

3. The container according to claim 1 wherein the cap comprises a closed end and an annular sidewall that extends from the closed end to an open end, the closed end and the annular sidewall collectively defining a cavity configured to hold a volume of the fluid, the closed end of the cap being flat so that the cap may be placed on a flat surface with the closed end resting on the flat surface.

4. The container according to claim 1 wherein the fluid is the oral care solution or water.

5. The container according to claim 1 wherein the sacrificial metal is zinc.

6. A container comprising;
a body adapted to contain an oral care solution; and
a cap selectively removable from the body, wherein the cap comprises:
   a cavity configured to contain a fluid;
   a first electrode comprising a sacrificial metal;
   a second electrode spaced from the first electrode; and
   an electrical connection electrically connecting the first electrode and the second electrode to a power source; and
wherein activation of the power source generates an electric field between the first and second electrodes, thereby causing the sacrificial metal of the first electrode to release ions into the fluid in the cavity of the cap; and
   wherein the cap comprises a base surface and an annular sidewall extending from the base surface, and wherein the first and second electrodes comprise metallic wire loops coupled to an inner surface of the annular sidewall in a spaced apart manner, the loops extending parallel to one another.

* * * * *